United States Patent [19]

Lee et al.

[11] Patent Number: 5,004,717
[45] Date of Patent: Apr. 2, 1991

[54] PROCESS FOR IN-SITU REGENERATION OF AGED METHANOL CATALYSTS

[75] Inventors: Sunggyu Lee, Akron, Ohio; Sawant Ashok, New Delhi, India; Conrad J. Kulik, Newark, Calif.

[73] Assignee: Electric Power Research Institute, Inc., Palo Alto, Calif.

[21] Appl. No.: 345,140

[22] Filed: Apr. 28, 1989

[51] Int. Cl.$^5$ .................. B01J 23/94; B01J 38/18; C07C 29/16
[52] U.S. Cl. ........................ 502/50; 502/49; 518/709; 518/713
[58] Field of Search .............. 502/50, 49, 53; 518/709, 713

[56] References Cited

U.S. PATENT DOCUMENTS

| | | | |
|---|---|---|---|
| 4,623,668 | 11/1986 | Broecker et al. | 502/38 |
| 4,801,574 | 1/1989 | Brown et al. | 502/30 |
| 4,855,267 | 8/1989 | Cheng | 502/50 |

*Primary Examiner*—Paul E. Konopka
*Attorney, Agent, or Firm*—Flehr, Hohbach, Test, Albritton & Herbert

[57] ABSTRACT

A process is provided for regenerating aged copper-containing coprecipitated methanol synthesis catalyst. The process includes treating the aged catalyst in an oxidizing atmosphere according to a specified time-temperature ramp, then in a reducing atmosphere. The oxidation-reduction cycle may be repeated as needed. An advantage of the invention is that the catalyst may be regenerated in situ in the same vessel in which the catalyst is utilized to make alcohol.

11 Claims, 3 Drawing Sheets

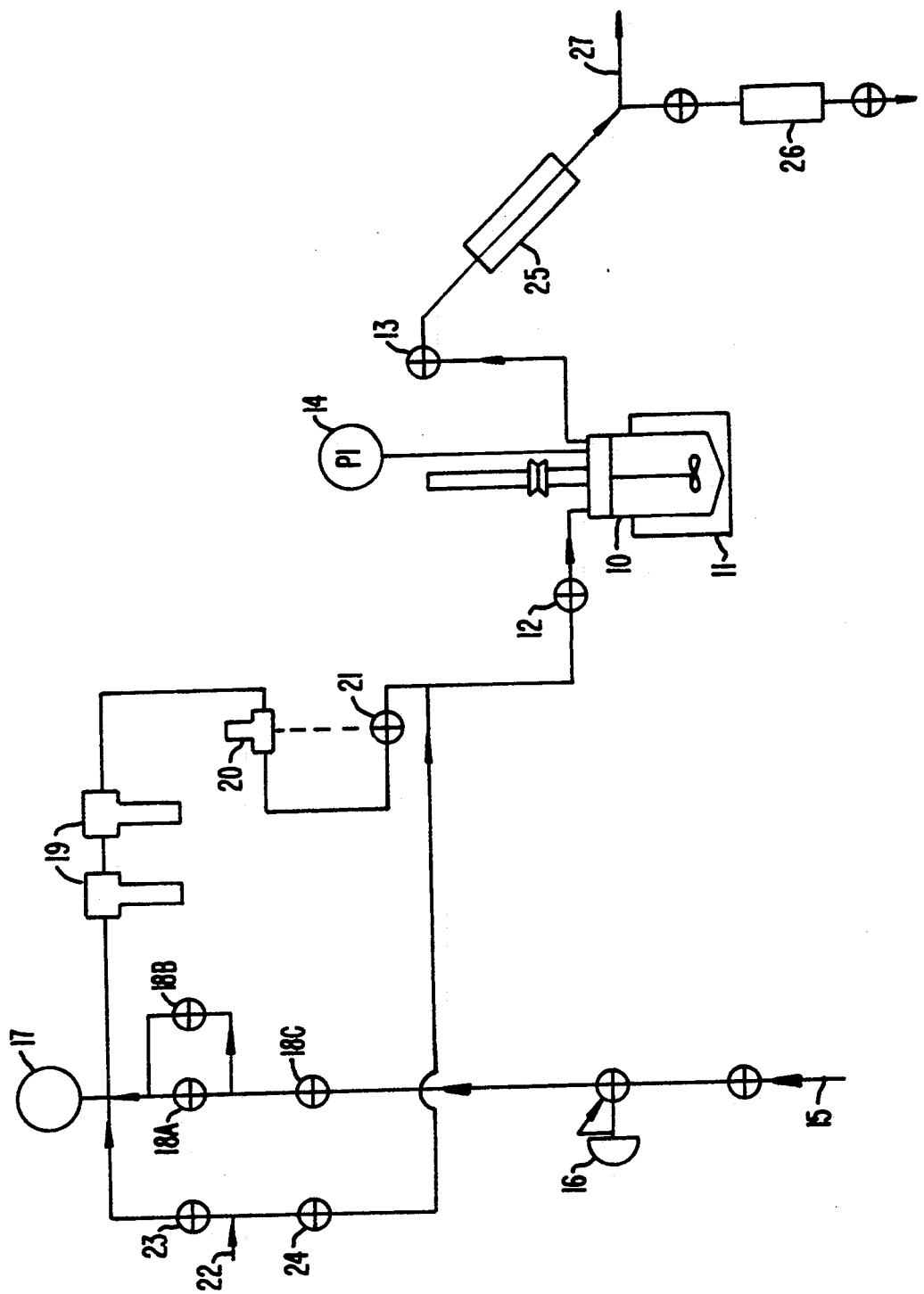
FIG._1.

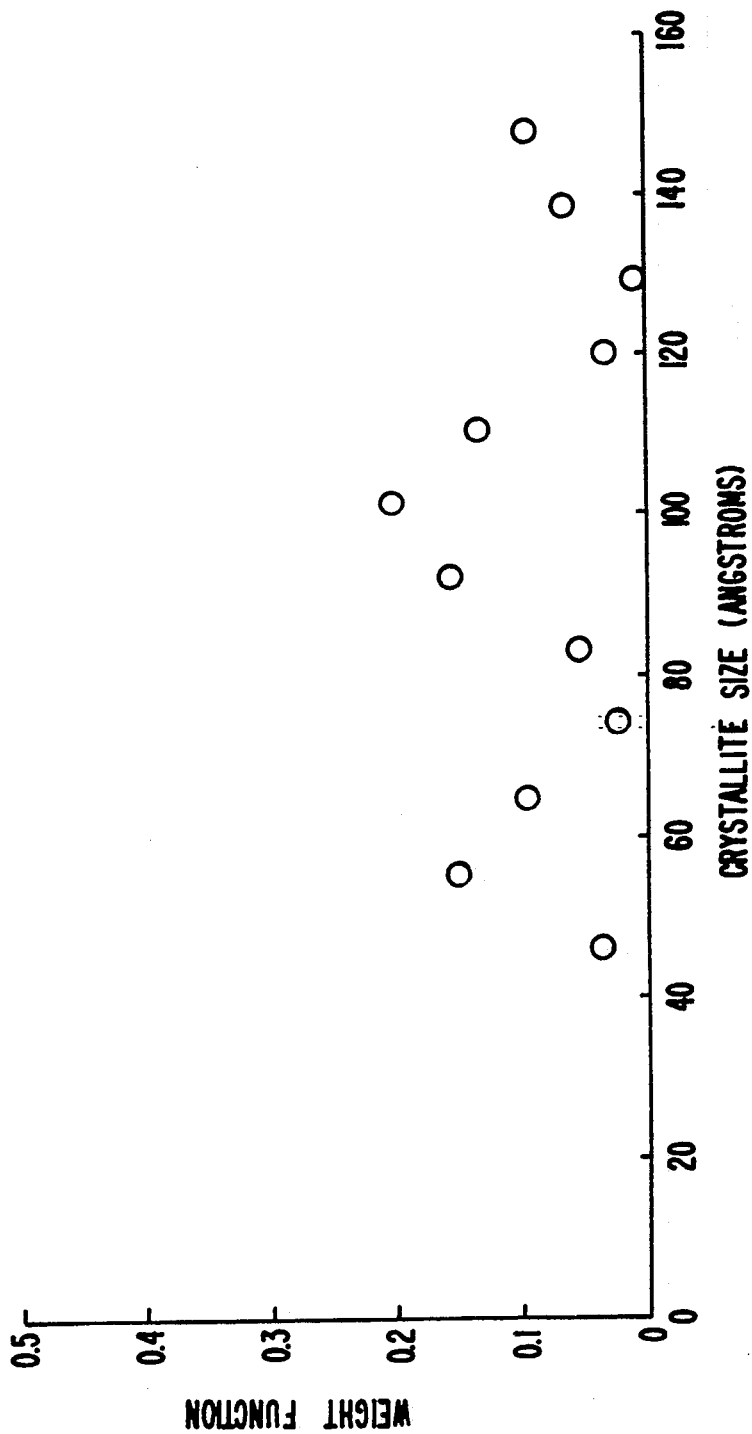

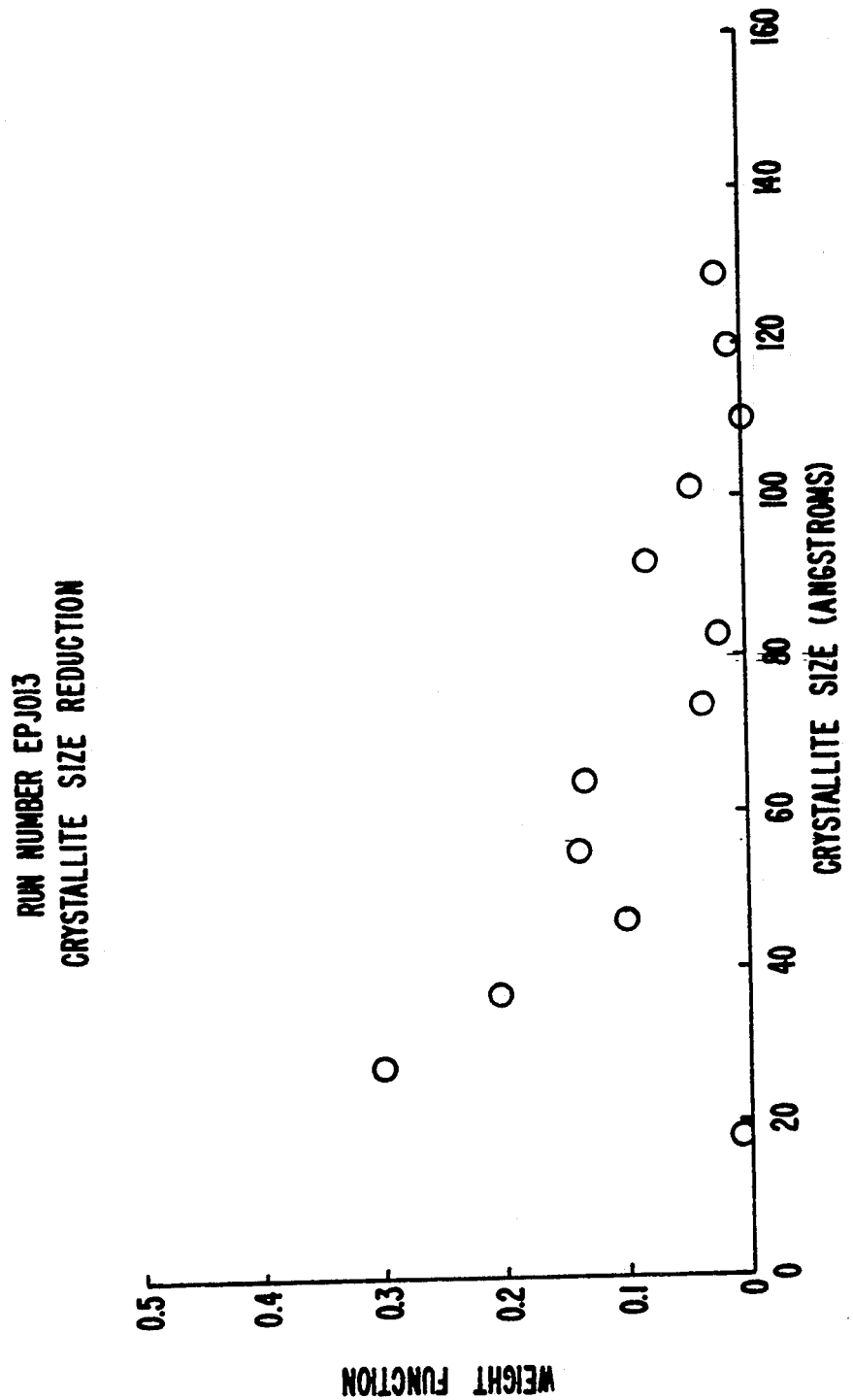
FIG._3.

PROCESS FOR IN-SITU REGENERATION OF AGED METHANOL CATALYSTS

The present invention relates to a process for regenerating an aged coprecipitated copper-containing catalyst used for catalytically converting hydrocarbon feed stock to alcohol, particularly methanol. The procedure comprises subjecting the aged catalyst to a series of increasing temperature oxidation steps in air or oxygen, followed by cooling and reduction by treatment with hydrogen or hydrogen containing gas. An advantage of the invention is that the catalyst may be regenerated in situ in the same vessel used for catalytic alcohol synthesis.

BACKGROUND OF THE INVENTION

Aged high pressure alcohol synthesis catalysts, particularly for methanol, which contain copper, suffer from a loss or substantial decrease of catalytic activity after use over an extended period of time. This degeneration of the catalyst is believed to be caused by the growth of the crystallite in the catalyst particles. A similar phenomenon has been observed in low pressure liquid phase methanol synthesis catalysts. The growth of the crystallites results primarily in a loss of active surface area, thereby decreasing the catalytic activity.

In the field of support-platinum catalysts (such as platinum-zeolite catalyst) there is a problem of agglomeration of the catalyst particles. Some approaches to remedying this problem include cascading hydrogen over the catalyst at a designated temperature and pressure and then cascading oxygen over the hydrogen-contacted catalyst at a designated temperature and pressure. See, for example, U.S. Pat. No. 4,689,312 to Le, et al. Methanol conversion catalysts, however, do not usually contain platinum or other group VIII metals. Furthermore, methanol catalysts are coprecipitates. In addition, in the case of the liquid phase methanol synthesis process, the catalysts during use are often in a liquid slurry which makes it difficult to separate from the oil in the slurry for regeneration. Furthermore, regeneration in situ, i.e., regeneration of a catalyst in the same vessel in which the catalytic process is conducted, is often dangerous since the equipment for conducting the catalytic process in many instances has not been designed to withstand the conditions required for regeneration. Accordingly, in many instances, in order to regenerate a catalyst it is necessary to transfer it from the vessel in which the catalytic reaction takes place to a different vessel for regeneration.

Therefore, there is a need for a method for regenerating copper-containing alcohol catalysts which is not only rapid and economical, but which can be conveniently and safely carried out in situ in the same vessel in which the catalytic process takes place.

SUMMARY OF THE INVENTION

The present invention provides a novel catalyst regeneration procedure for copper-containing alcohol catalysts. The catalysts will be referred to hereinafter as methanol catalysts as a preferred embodiment. It has unexpectedly been found that copper-containing methanol catalyst may be regenerated, advantageously in situ in the same vessel in which the catalytic reaction takes place, by first oxidizing the aged catalyst by contact with an oxidizing atmosphere containing air or oxygen at a temperature in the range of about 15° to 35° C. for about 1 to 2 hours, continuing the contacting at a second temperature in the range of 40° to 70° C. for about 3 to 5 hours, continuing the contacting at a third temperature in the range of about 130° to 170° C. for 2 to 5 hours, and completing the oxidation at a temperature in the range of about 190° to 230° C. for about 2 to 4 hours; then contacting the aged and oxidized catalyst with a stream of inert gas and allowing the catalyst to cool to a temperature below about 150° C.; then reducing the aged catalyst by contact with a reducing gas stream comprising hydrogen gas for a period of time and at a temperature sufficient to reduce the copper oxides. Optionally, the process may be repeated until the catalyst has been regenerated to a level of sufficient catalytic activity.

BRIEF DESCRIPTION OF THE DRAWINGS

FIG. 1 shows the diagram of an apparatus for utilizing the process in accordance with the present invention.

FIG. 2 shows the crystallite size distribution of a copper-containing methanol catalyst which has been aged in a carbon monoxide-free atmosphere prior to the regenerative treatment according to the present invention.

FIG. 3 shows the crystallite size distribution of the catalyst from FIG. 2 which has been regenerated in accordance with the present invention.

DETAILED DESCRIPTION OF THE INVENTION

Catalyst compositions used for conversion of hydrocarbon feed stock (such as syngas) to alcohols (such as methanol) are copper-containing and usually comprise, initially in their unreduced form, copper oxide, zinc oxide and alumina or titania. These catalysts are formed by coprecipitation processes. Prior to use, they are normally activated by treatment in a reducing atmosphere containing gases such as hydrogen to convert them to their active form at reduced oxidation levels of copper, zinc oxide and alumina (or titania). Over a period of time during the use of these catalysts, the activity of the catalysts substantially decreases, which is not believed to be due to coking as in other hydrocarbon conversion processes using platinum-zeolites, but rather to the growth of the crystallites in the catalytic particles.

Accordingly, it is an object of the present invention to provide a process for regenerating such copper-containing catalysts.

It is another object of the invention to provide a method for regenerating methanol catalysts which are copper-containing, which process may be conducted in situ in the same vessel in which the catalytic process is conducted.

These and other objects will be apparent from the following description and from the practice of the invention.

In accordance with the present invention, an aged copper-containing methanol synthesis coprecipitated catalyst, either in solid or in a liquid slurry, preferably in the same vessel in which the catalytic process is carried out, is regenerated by a process comprising the steps of:

Oxidizing the aged catalyst using an oxidizing atmosphere comprising oxygen and/or air under the following conditions. The following conditions are important since if they are not carefully followed, the highly exothermic reactions of formation of the oxides of copper produce excess of heat and may irreparably damage a catalyst, and/or cause a runaway reaction within the vessel. Since typically the vessel which contains the catalyst will not be designed specifically for the regeneration process, but rather for the alcohol synthesis process, it is important that the oxidation be under control at all times in accordance with the conditions prescribed by the present invention. The following temperature program is provided as a preferred embodiment. It will be appreciated by those in the art that the following preferred temperature program can be readily altered to accommodate higher density of catalyst. In such a case, a longer period of time for each temperature step will be utilized. According to the present invention, the aged catalyst is preferably first oxidized by contact with an oxidizing gas stream containing oxygen at a first oxidation temperature in the range of about 15° to 35° C. for a period of time in the range of about 1 to 2 hours, and preferably this temperature should be about 25° C. and maintained for about 1.5 hours. Then, while still being in contact with the oxidizing gas stream, the temperature is raised to a second oxidation temperature in the range of about 40° to 70° C. and is maintained for about 3 to 5 hours. This second temperature is preferably in the range of about 50° to 60° C. and is maintained preferably for about 4 hours. Then, again while still in contact with the oxidizing gas stream, the temperature is raised to a third oxidizing temperature in the range of about 130° to 170° C. for about 2 to 5 hours. Preferably this third oxidation temperature is about 150° C. and is maintained for about 3.5 hours. Finally, while still in contact with the oxidizing gas stream, the temperature is raised to a fourth oxidation temperature in the range of about 190° to 230° C. for about 2 to 4 hours. Preferably this fourth oxidation temperature is about 210° C. and is maintained for about 3 hours. The gradual increase of temperature during exposure to the oxidizing gas stream is important to avoid damage to the catalyst and to control the reaction conditions within the vessel.

Following the oxidation, the oxidizing gas stream is ceased and the catalyst is purged and contacted with an inert gas, such as nitrogen or argon, and the catalyst is allowed to cool to a temperature below about 150° C. This cooling is important, since the oxidized catalyst should have proper environments to settle in terms of its structure after the induced phase change. After cooling, the aged catalyst is then contacted with a reducing gas stream comprising hydrogen gas for a period of time and at a temperature sufficient to reduce the copper oxides.

Preferred reducing conditions are those disclosed by Sawant et al., *Fuel Science & Technol. Int'L*, 5(1), 77-88 (1987), which is incorporated by reference herein. Typically, the reducing conditions will comprise flowing a stream comprising about 2-10% (volume) hydrogen in an inert gas, such as argon or nitrogen, through a slurry (typically 200 g. catalyst/liter oil) at room temperature and pressure. The completion of reduction can be indicated by the cessation of water condensation from the gases exiting the reactor and also by the stabilization of the reactor temperature.

Optionally, the above oxidation-cooling-reduction steps are repeated until the catalyst has been regenerated to attain a level of sufficient catalytic activity.

In the above-described process the oxidizing gas stream may be air or oxygen and reducing gas stream may be hydrogen. Alternatively, other oxidizing agents such as carbon dioxide may be used as an oxidation gas and other reducing agents such as carbon monoxide as the reducing gas.

In the oxygen contact stage, the aged catalyst is contacted with oxygen alone, air, oxygen admixed with an inert gas such as nitrogen. Air is the preferred oxidizing gas. The air pressure and flow rate will depend in part on the size of the reactor containing the catalyst, the volume of the aged catalyst, and the physical state of the catalyst (i.e., as a solid or a liquid slurry). The air flow rate can range usually from about 0.5 to 3 slpm per one liter capacity of conventional reactor volume under pressures which can range from 10 to 50 psig.

In the reducing stage, the aged catalyst will be subjected to hydrogen at a flow rate in the range of about 0.5 to 3 slpm under atmospheric pressure, which parameters again depend upon the size of the reactor vessel, the volume of catalyst needed to be regenerated and the physical state of the catalyst. Preferably hydrogen is used and may be taken from any of the hydrogen streams in a typical refinery, such as from the hydrogen recycle stream or from the stream of a steam reformer. Typically refinery streams will have a hydrogen concentration greater than 50 volume percent, with the remainder being inert gas. The hydrogen stream, however, should not contain any sulfur compounds, although it may contain inert gases such as nitrogen or carbon monoxide and lower hydrocarbons.

A particular advantage of the present invention is that the average crystallite size in the catalyst, subsequent to regenerative treatment according to the present invention, is reduced by at least about 50%, and often very close to the original size, thus enhancing the surface area and therefore the catalytic activity.

Referring to FIG. 1, there is shown an apparatus for utilizing the process according to the present invention. The apparatus shown in FIG. 1 is particularly adapted to analyze condensable products made in the reactor. Referring to FIG. 1, the reactor 10 containing the slurry of catalyst is equipped with an agitator and heated by an appropriate heating means 11. The reactor is closed to the atmosphere for pressurizing via valves 12 and 13 where pressure is monitored by pressure indicator 14. During normal operation of the reactor for alcohol synthesis, the syngas or other hydrocarbon feed stock is fed through inlet line 15, the pressure of which is initially regulated by pressure regulator 16, monitored by pressure indicator 17. The flow may be regulated by appropriate safety and check valves 18A, B and C. The gas is filtered, preferably through a plurality of filtering means 19, and the flow into reactor 10 is controlled by a flow sensor 20 which automatically controls the control valve 21. If required, inert gas such as nitrogen which is fed in through line 22 may be added to the gas flow either upstream of the filters 19 via valve 23 or downstream of the filters 19 via valve 24. The catalytic reaction producing the alcohol is run under the desired controlled conditions of temperature and pressure within the reactor 10 and the products may be withdrawn therefrom through valve 13. Liquid products are condensed in condenser 25 and collected into liquid product collector 26. The non-condensable products exit through line 27 for further treatment, analysis, and the like. When the catalyst slurry within reactor 10 becomes substantially aged so that its catalytic activity is at a level which is no longer desirable, the catalyst may be regenerated in situ. All the residual syngas is purged from the system by opening valves 23, 24, 12 and 13. Then air or other oxidizing gas is introduced at the inlet 15. If needed, nitrogen may be added to the air flow either upstream or downstream of the filters via valves 23 and 24. The air stream is allowed to flow through the reactor 10 while the reactor is at the temperatures described above for the oxidation step. After the oxidation is completed, nitrogen is again flowed through the system, including the reactor 10, while the reactor is allowed to cool below a temperature of about 150° C. Then hydrogen (or other reducing gas such as carbon monoxide) is introduced through inlet 15 and allowed to flow through the reactor 10 under the conditions described above. If the process is to be repeated, the system may be again purged with nitrogen, then the oxygen (or other oxidizing gas) flowed through the system, followed by purging and cooling with nitrogen, and treatment with the reducing gas. These treatments are continued until the desired activity of the catalyst within the reactor 10 is regenerated, after which the reactor may then be utilized for production of the alcohol.

The following example is provided by way of illustration and is not intended to limit the invention in any way.

EXAMPLE 1

An experiment was carried out on a batch of EPJ-19 catalyst (manufactured United Catalysts, Inc., CuO/ZnO/alumina in unreduced form) which had been aged. The specific catalyst batch was designated as EPJ903. To simulate ageing, this catalyst batch was run with a gas feed containing no CO in a 1-liter autoclave, and the operating conditions are given in Table 1.

TABLE 1

| Catalyst Batch | Operating Mode | T (C) | P (psia) | Time Hours | Average Crystallite Size |
|---|---|---|---|---|---|
| EPJ903 | Continuous | 250 | 1015 | 60 | 105.5 A |

The average Cu (111) crystallite size of 105.5 A is quite large compared to that of freshly reduced catalyst, 29.5 A. The catalytic activity of EPJ903 is also significantly lower than that of freshly reduced catalyst.

A catalyst slurry of aged catalysts was loaded into the autoclave and oxidized with compressed air and re-reduced following the parameters in Table 2.

TABLE 2

| Catalyst Regeneration Process Via Crystallite Redispersion | |
|---|---|
| Oxidation Process Conditions: | |
| Oxidizing gas; | Air |
| Pressure; | 10 psig |
| Gas flow; | 1 SLPM/1 liter reactor |
| Impeller speed; | 1500 RPM |
| Reactor; | Slurry reactor |
| Procedure: | |
| (1) Oxidize at 25° C. for 1.5 hours | |
| (2) Oxidize at 50–60° C. for 4 hours | |
| (3) Oxidize at 150° C. for 3.5 hours | |
| (4) Keep at 210° C. for 3 hours | |
| (5) Switch to inert gas (N$_2$) and cool before reduction | |
| (6) Re-reduce the catalyst by the procedure described by Sawant, et al., Fuel Science & Technol. Int., 5 (1), 77–88 (1987), which is incorporated by reference herein. | |
| (7) Repeat the steps (1)–(6), if necessary | |

The air pressure should be kept relatively low because of the danger of spontaneous combustion of the oil in the slurry. The Cu (111) reflection was analyzed by line profile analysis in order to determine the crystallite size distribution and the average size of the treated catalyst. The line profile analyses of X-ray diffraction patterns of the aged and treated catalysts are shown in FIGS. 2 and 3, respectively. As very clearly shown, there was a dramatic decline in the average crystallite size.

The average crystallite size shifts from 105.5 A to 53.5 A, even within a single treatment cycle. The crystallite size distribution is also seen to shift towards lower size ranges. The recovery of the activity was from 71% of the initial activity in the aged catalyst to 97% of initial activity in the regenerated catalyst.

While specific embodiments of the present invention have been shown and described, it will be apparent that many modifications may be made thereto without departing from the spirit and scope of the invention. Accordingly, the invention is not limited to the foregoing description, but is limited only by the scope of the claims appended hereto.

We claim:

1. A process for regenerating an aged alcohol synthesis catalyst comprising coprecipitated copper-containing crystallites, whereby the average crystallite size is reduced by at least about 50% comprising the steps of:
   A. Oxidizing said aged catalyst by contact with an oxidizing gas stream comprising oxygen at a first oxidation temperature in the range of about 15° to 35° C. for about 1 to 2 hours; then at a second oxidation temperature in the range of about 40° to 70° C. for about 3 to 5 hours; then at a third oxidation temperature in the range of about 130° to 170° C. for about 2 to 5 hours; then at a fourth oxidation temperature in the range of about 190° to 230° C. for about 2 to 4 hours;
   B. Contacting said aged catalyst with a stream of inert gas and allowing said aged catalyst to cool below a temperature of about 150° C.;
   C. Reducing said aged catalyst by contact with a reducing gas stream for a period of time and at a temperature sufficient to reduce copper oxides contained in said catalyst and wherein the gas streams in steps A, B and C are added at flow rates of about 0.5 to about 3 SLPM/liter of reactor volume.

2. A process according to claim 1 wherein said oxidizing gas stream comprises air.

3. A process according to claim 1 wherein said reducing gas comprises molecular hydrogen.

4. A process according to claim 3 wherein said reducing gas comprises carbon monoxide.

5. A process according to claim 3 wherein said reducing gas comprises feed stock syngas for methanol synthesis.

6. A process according to claim 1 wherein in Step A said first oxidation temperature is about 25° C. and is maintained for about 1.5 hours; said second oxidation temperature is in the range of about 50° to 60° C. and is maintained for about 4 hours; said third oxidation temperature is about 150° C. and is maintained for about 3.5 hours; and said fourth oxidation temperature is about 210° C. and is maintained for about 3 hours.

7. A process according to claim 1 wherein said reducing temperature is in the range of 120° to 250° C.

8. A process according to claim 1 wherein said catalyst comprises in its active form a coprecipitate comprising copper, zinc oxide and alumina.

9. A process according to claim 1 wherein said process is conducted within the same vessel in which said catalyst is utilized for the catalytic conversion of hydrocarbon feed stock to alcohol.

10. A process according to claim 1 wherein said aged catalyst is subjected to a sufficient number of repetitions of said process to reduce the average crystallite size in said catalyst by at least about 50%.

11. A process according to claim 10 wherein said average crystallite size is reduced to approximately its original size.

* * * * *